United States Patent
Franklin et al.

(10) Patent No.: US 8,196,497 B2
(45) Date of Patent: Jun. 12, 2012

(54) SYSTEM AND METHOD FOR CONTROLLING THE LENGTH OF A DISCRETE SEGMENT OF A CONTINUOUS WEB OF ELASTIC MATERIAL

(75) Inventors: Kent A. Franklin, Neenah, WI (US); Gary P. Strike, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 13/005,873

(22) Filed: Jan. 13, 2011

(65) Prior Publication Data

US 2011/0174123 A1 Jul. 21, 2011

Related U.S. Application Data

(62) Division of application No. 11/849,038, filed on Aug. 31, 2007, now Pat. No. 7,891,276.

(51) Int. Cl.
*B23Q 15/00* (2006.01)

(52) U.S. Cl. .................... 83/13; 83/74; 83/358; 83/949; 83/72

(58) Field of Classification Search ................ 83/37, 42, 83/74, 312, 358, 949, 72, 13
See application file for complete search history.

(56) References Cited

U.S. PATENT DOCUMENTS

| | | |
|---|---|---|
| 3,933,035 A | 1/1976 | Roch |
| 4,004,510 A | 1/1977 | Roch |
| 4,052,019 A | 10/1977 | Dickson, Jr. |
| 4,170,155 A | 10/1979 | Saito et al. |
| 4,369,906 A | 1/1983 | Isherwood |
| 4,663,220 A | 5/1987 | Wisneski et al. |
| 4,724,732 A | 2/1988 | Miyauchi et al. |
| 4,940,464 A | 7/1990 | Van Gompel et al. |
| 4,947,336 A | 8/1990 | Froyd |
| 4,990,840 A | 2/1991 | Migda |
| 5,046,272 A | 9/1991 | Vogt et al. |
| 5,095,219 A | 3/1992 | Laumann et al. |

(Continued)

FOREIGN PATENT DOCUMENTS

EP 0217032 4/1987

(Continued)

OTHER PUBLICATIONS

International Search Report & Written Opinion from PCT/IB2008/053275, dated Jan. 23, 2009, 11 pages.

*Primary Examiner* — Boyer D. Ashley
*Assistant Examiner* — Omar Flores Sanchez
(74) *Attorney, Agent, or Firm* — Armstrong Teasdale LLP

(57) ABSTRACT

In a system and method for controlling the length of a discrete segment of an elastic web, a wound off tension of the web is determined during unwinding from a wound roll. The unwound web is delivered to a processing station while being maintained in tension. A discrete segment of the web is transported away from the processing station for at least a time t wherein the discrete segment decreases in length to a recovered length. The recovered length is predicted based at least in part on the wound off tension and in response to the predicted recovered length, at least one of the following is controlled: 1) the speed at which the web is delivered to the processing station, 2) the tension in the continuous web as it is delivered to the processing station, and 3) the length of the discrete segment at the processing station.

11 Claims, 6 Drawing Sheets

U.S. PATENT DOCUMENTS

| | | | |
|---|---|---|---|
| 5,103,679 A | 4/1992 | Porter et al. |
| 5,104,116 A | 4/1992 | Pohjola |
| 5,224,405 A | 7/1993 | Pohjola |
| 5,226,992 A | 7/1993 | Morman |
| 5,286,317 A | 2/1994 | Treat et al. |
| 5,308,010 A | 5/1994 | Hakiel |
| 5,485,386 A | 1/1996 | Andreasson |
| 5,550,685 A | 8/1996 | Drouin |
| 5,709,331 A | 1/1998 | Lam et al. |
| 5,765,482 A | 6/1998 | Wittkopf et al. |
| 5,930,139 A | 7/1999 | Chapdelaine et al. |
| 5,932,039 A | 8/1999 | Popp et al. |
| 5,952,804 A | 9/1999 | Hamamura et al. |
| 6,092,466 A | 7/2000 | Koch et al. |
| 6,147,468 A | 11/2000 | Hamamura et al. |
| 6,470,225 B1 | 10/2002 | Yutkowitz |
| 6,473,669 B2 | 10/2002 | Rajala et al. |
| 6,517,679 B1 | 2/2003 | Mustonen et al. |
| 6,547,707 B2 | 4/2003 | Cote |
| 6,555,987 B2 | 4/2003 | Leenhouts |
| 6,652,686 B1 | 11/2003 | Coenen et al. |
| 6,677,722 B2 | 1/2004 | Hamamura et al. |
| 6,781,339 B1 | 8/2004 | Ikeguchi |
| 6,845,282 B2 | 1/2005 | Franz |
| 6,851,593 B2 | 2/2005 | Weber et al. |
| 6,916,750 B2 | 7/2005 | Thomas et al. |
| 6,991,144 B2 | 1/2006 | Franz et al. |
| 6,993,964 B2 | 2/2006 | Franz et al. |
| 7,004,053 B1 | 2/2006 | Franklin et al. |
| 2003/0078684 A1 | 4/2003 | Martin et al. |
| 2003/0188965 A1 | 10/2003 | King et al. |

FOREIGN PATENT DOCUMENTS

| | | |
|---|---|---|
| JP | 5665751 | 6/1981 |
| JP | 61111262 | 5/1986 |
| JP | 62280154 | 12/1987 |
| JP | 280657 | 3/1990 |
| JP | 2100105 | 4/1990 |
| JP | 04182250 | 6/1992 |
| JP | 6297385 | 10/1994 |
| JP | 895643 | 4/1996 |
| JP | 09040247 | 2/1997 |
| JP | 10250888 | 9/1998 |
| JP | 2000172341 | 6/2000 |
| WO | 0101211 | 1/2001 |
| WO | 02086456 | 10/2002 |
| WO | 03035526 | 5/2003 |
| WO | 03085183 | 10/2003 |

SYSTEM AND METHOD FOR CONTROLLING THE LENGTH OF A DISCRETE SEGMENT OF A CONTINUOUS WEB OF ELASTIC MATERIAL

CROSS REFERENCE TO RELATED APPLICATION

This application is a divisional application of U.S. patent application Ser. No. 11/849,038, filed Aug. 31, 2007, which is hereby incorporated by reference in its entirety.

FIELD OF INVENTION

This invention relates generally to the handling of continuous webs of elastic material, and more particularly to a system and method for controlling the length of a web segment of the continuous web of elastic material.

BACKGROUND

A number of different handling processes are used to process continuous webs of elastic material into defined segments, such as discrete webs cut from a continuous web for subsequent processing. For example, such discrete webs of elastic material are commonly used as components in the assembly of diapers, training pants and other disposable absorbent garments. As a further example, the side panels of such absorbent garments are typically discrete webs of elastic material. In general, the absorbent garment manufacturing line in which the discrete webs are used comprise a pre-wound roll of the continuous elastic material that is unwound by a suitable drive mechanism and fed (often through various stations of the manufacturing line) to a cutting station at which the web is cut sequentially into discrete webs of the elastic material. Typically the continuous web is held in tension as it is transported from the wound roll to the cutting station so that the web is elongated to some extent. The discrete webs are then transported away from the cutting station to another station of the manufacturing line at which the discrete webs are placed on and assembled with other components of the absorbent garment being formed.

Research has shown that the stretchability (i.e., the ability of the web to elongate under tension) of a continuous web that is pre-wound on a wound roll of the web material may vary throughout the roll (i.e., from the beginning to the end of the roll, or throughout the radius of the roll), and from one roll to the next. For example, if a discrete web is cut from a segment of the beginning of a roll under a particular tension (e.g., at the cutting station), and another discrete web is later cut from a segment elsewhere (e.g., the middle or the end) on the roll under that same tension, the cut lengths may be different due to variant stretchability at different segments of the continuous web.

Accordingly, existing elastic web handling processes and, in particular, absorbent garment manufacturing lines often include some type of control system and/or method for detecting the cut length of the discrete webs and correcting the cut length when cut length errors are detected. For example, a feedback-type control system relies on a cut length error (i.e., the difference between a measured cut length of the discrete web and a target cut length) to determine the magnitude of a processing correction. Other known systems and methods utilize what is referred to as a feed-forward control system that predicts what the cut length will be based on conditions of the web prior to cutting, and when necessary adjusts the feed rate, web tension or other properties based on the predicted cut length. For example, in one such process registration marks on the continuous web are used to measure the distance therebetween just prior to cutting and to predict the cut length of the discrete webs based on this measurement. By comparing the predicted cut length to a target cut length, the manufacturing line is adjusted by the control system to change the predicted cut length so as to more closely match the target cut length.

However, when dealing with an elastic web that is under tension (and more particularly, stretched) upon being fed to the cutting station, the discrete webs will retract, or recover after being cut since they are no longer under tension. In particular, due to elastic effects the discrete webs will recover in some measure relatively quickly following cutting, and due to visco-elastic effects will further recover more slowly so that at a time t after being cut the length (i.e., the machine direction dimension) of the discrete web will have decreased. A similar effect is experienced in defined segments of the continuous web, such as between registration marks, where processing of the continuous web involves stretching the web and subsequently reducing or removing the stretching forces from the continuous web.

In prior web handling processes such as those described above, the "cut length" or "segment length" measured or predicted (and relied upon) by the control system manufacturing line is the length of continuous web that is actually cut at the cutting station, or other processed at a particular station in its stretched condition, not the length following recovery under reduced or zero tension some time t after cutting or processing. Thus, such a control system does not take into account the role that changes in elastic and visco-elastic effects have on the discrete webs or web segments as they are transported from the cutting or processing station to further processing stations. Instead, a particular uniform amount of recovery of the discrete web is presumed.

It is known, though, that the pre-wound continuous web of elastic material is subjected to both radial and circumferential stress that varies throughout the wound roll of web material, typically due to existing winding processes and the changing size of the roll from the first wind to the last. Because the continuous web may remain in this condition for a prolonged period of time before being used in the absorbent garment manufacturing line, the visco-elastic properties of the web can change (e.g., resulting in the web being partially or wholly set in a more elongated condition) and indeed may vary substantially throughout the radius of the roll of web material, or from one roll to the next. Thus, after a time t following cutting (or segment processing between registration marks), discrete webs cut from one segment of the wound continuous web may not recover as much as, or may recover more than, discrete webs cut from another segment of the wound continuous web. This can occur even if the cutting length at the cutting station is the same for the discrete webs because the permanent or partial set in the wound web varies throughout the web but the tension in the web at the time of cutting is generally uniform.

There is a need, therefore, for a system and method of controlling the length of a discrete web of elastic material at a time t following cutting of the discrete web from a wound roll of continuous web, and/or controlling the length of a segment of a continuous web of elastic material at a time t following a particular processing step, and more suitably such a system and method which takes into account both the visco-elastic and elastic conditions of the continuous web of material prior to cutting or prior to the particular processing step.

SUMMARY

In one embodiment, a method of controlling the length of a discrete segment of an elastic web in a web handling system generally comprises unwinding a continuous web of elastic material from a wound roll of the continuous web. A wound off tension of the continuous web is determined as the continuous web is being unwound from the wound roll. The unwound continuous web is delivered in a machine direction from the wound roll to a processing station while maintaining the web in tension for at least part of the distance traveled by the web from the wound roll to the processing station, with a discrete segment of the web having a segment length at the processing station. The discrete web is transported away from the processing station along the machine direction for at least a time t wherein the discrete segment decreases in machine direction length from the segment length to a recovered length after leaving the processing station. The recovered length of the discrete segment at the time t after leaving the processing station is predicted based at least in part on said wound off tension of the continuous web. In response to the predicted recovered length of the discrete segment, at least one of the following is controlled: 1) the speed at which the continuous web is delivered from the wound roll to the processing station, 2) the tension in the continuous web as the web is delivered from the wound roll to the processing station, and 3) the segment length of the discrete segment at the processing station.

BRIEF DESCRIPTION OF THE DRAWINGS

Corresponding reference characters indicate corresponding parts throughout the drawings.

DETAILED DESCRIPTION

Figure 1:
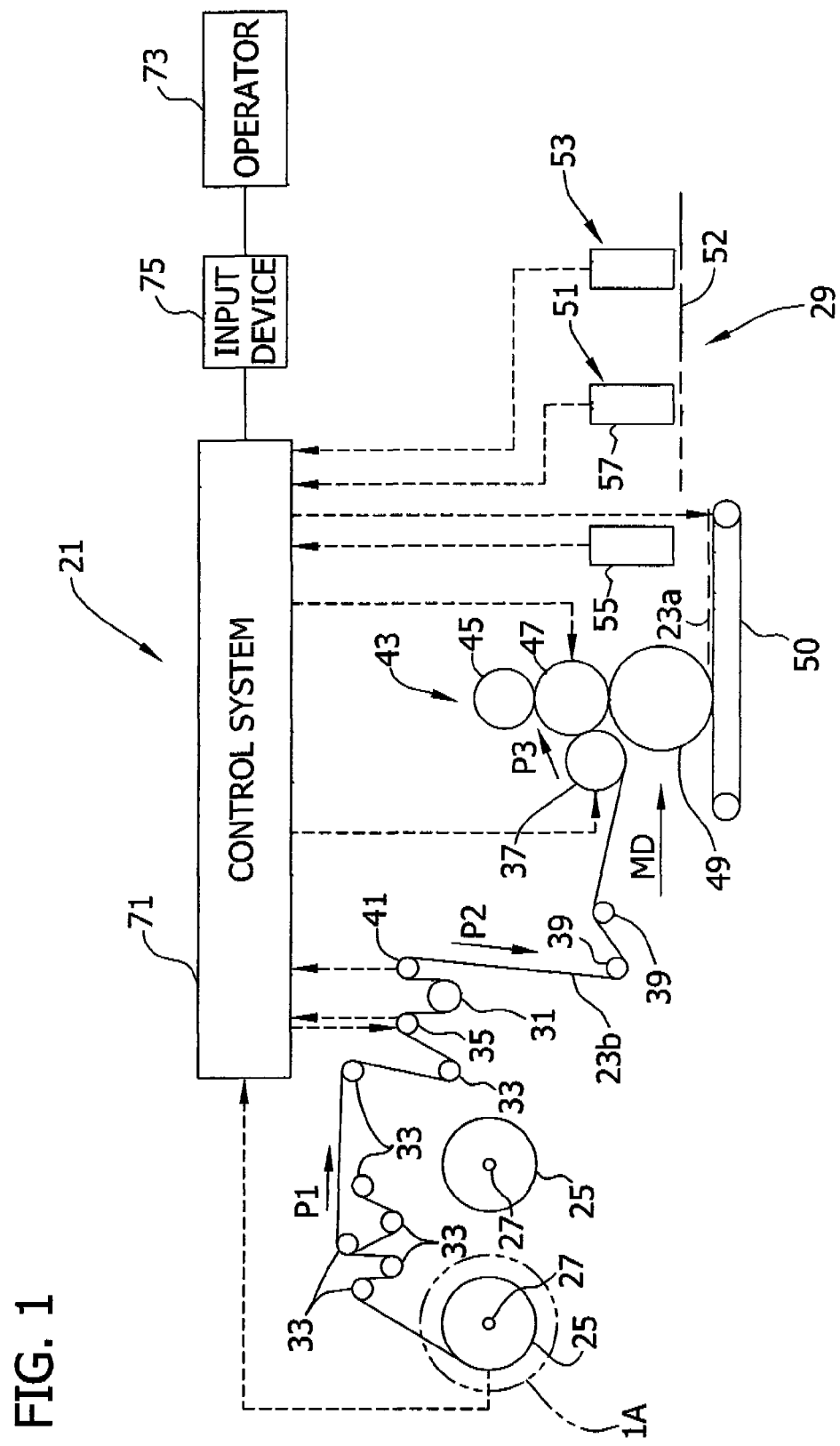
FIG. 1 is a schematic of one embodiment of a web handling system for controlling the length of a discrete web of material cut from a continuous web of elastic material.

With reference now to the drawings, FIG. 1 is a schematic diagram of one example of a web handling system, generally indicated at 21, for controlling the length of discrete webs 23a of elastic material at a time t after the webs are cut from a continuous web 23b of elastic material, and more particularly from a wound roll 25 of such a continuous web of elastic material. The illustrated web handling system 21 suitably feeds a disposable absorbent garment manufacturing line (a portion of which is indicated generally at 29 in FIG. 1) in which various components of the garment are assembled together as the components, and hence the garment at various stages of assembly thereof, are moved through the manufacturing line in a machine direction MD. Examples of such disposable absorbent garments include, without limitation, diapers, training pants, adult incontinence products, feminine care products and the like. In the illustrated embodiment, the discrete webs 23a formed by the web handling system 21 are used as side panels of a pair of training pants and are fastened to the moving training pants assembly at a side panel fastening station 51 of the manufacturing line 29.

It is understood, however, that the web handling system 21 and methods described herein may be used by itself to produce discrete webs, or to feed a manufacturing line for making articles other than disposable absorbent garments, and remain within the scope of this invention. As used herein, the term "machine direction" refers to the direction in which the web 23b (and discrete webs 23a after cutting) are moved through the web handling system 21. The term "cross-machine" direction refers to a direction that is generally orthogonal to the machine direction MD and in the plane of the web 23a, 23b.

While the system and methods illustrated and described herein are for a web handling system 21 in which a continuous web is cut into discrete segments of web material, it is also understood that the web handling system and methods described herein may be used to control the length of particular segments (e.g., discrete segments) of a continuous web of elastic material, such as between registration marks or other markers on a continuous web, following processing of the web during which the web is tensioned and subsequently released in whole or in part from such tension. Accordingly, the term "discrete segment" as used herein is taken to refer to a cut segment of web material cut from a continuous web or to a defined segment of web material (e.g., between registration marks or other markers) along a continuous web.

Suitable elastic materials from which the web 23a, 23b may be formed, as well as one example of a suitable process for incorporating elastic side panels into an absorbent garment, are described in the following U.S. Pat. Nos. 4,940,464 issued Jul. 10, 1990 to Van Gompel et al.; 5,224,405 issued Jul. 6, 1993 to Pohjola; 5,104,116 issued Apr. 14, 1992 to Pohjola; and 5,046,272 issued Sep. 10, 1991 to Vogt et al.; all of which are incorporated herein by reference. As an example, suitable elastic materials include a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference.

As used herein, the term "stretchable" refers to a material that may be extensible and/or elastic. That is, the material may be extended, deformed or the like, without breaking, and may or may not significantly retract (i.e., recover) after removal of an elongating force. The term "elastic" refers to that property of a material where upon removal of an elongating force the material is capable of substantially recovering its original size and shape or exhibits a significant retractive force. As used herein, an elastic material is intended to refer to a material that exhibits elastic and/or viscoelastic behavior. The term "viscoelastic" is used herein to refer to that property of a material which is viscous but which also exhibits certain elastic properties such as the ability to store energy of deformation, and in which the application of a stress gives rise to a strain that approaches its equilibrium value slowly.

The web handling system 21 suitably includes an unwind spindle 27 (broadly, an unwind device) on which the wound roll 25 of the continuous web 23b of elastic material is mounted. The illustrated system 21 particularly includes a second unwind spindle 27 and another wound roll 25 of continuous web 23b of elastic material. With this arrangement, when one of the rolls 25 is completely unwound and in need of replacement the system 21 draws from the other wound roll while the unwound roll is being replaced. It is understood, however, that a single unwind device and wound roll 25 may be used without departing from the scope of this invention. It is also contemplated that two or more webs 23b may be drawn from respective wound rolls and laminated or otherwise secured together to form a continuous web of elastic material prior to the web being cut into discrete webs 23a.

A suitable drive mechanism, such as in the form of a rotatably driven drive roll 31 operates to draw the continuous web 23b from the wound roll 25 (thereby unwinding the wound roll) to move the web in the machine direction MD along a first path P1 of the system 21. The unwind spindle 27, according to one embodiment, may also be driven. As the continuous web 23b is unwound from the wound roll 25, it is drawn along the path P1 over a series of guide rolls 33 (also sometimes referred to as stationary rolls, or idler rolls) and then over a dancer roll 35 (broadly, a web tension control) before reaching the drive roll 31. A dancer roll 35 is commonly used to control tension in a moving web within a predetermined range of tensions. For example, while the web tension is intended to remain generally constant, it may vary due to factors such as non-uniform web properties, uneven wound rolls or web misalignment, speed changes in the drive roll and other factors. The dancer roll 35 may also be used for monitoring the tension in the web 23b as the web is drawn from the wound roll 25 to the drive roll 31 (e.g., based on the pre-determined tension range within which the dancer roll is initially set to maintain the web in tension).

It is contemplated that other web tension controls may be used to control the tension in the moving web 23b after the web is drawn from the wound roll 25. For example, a festoon (not shown) may be used instead of, or in addition to, the dancer roll 31 to control (including monitor) the tension in the web 23b.

The rotational speed of the drive roll 31 generally determines the machine direction MD speed of the web 23b as it moves along the path P1 from the wound roll 25 to the drive roll. Tension in the continuous web 23b along the path P1 is also at least in part a function of the rotational speed of the unwind spindle 27 if the spindle is driven (i.e., a function of the differential between the drive roll rotational speed and the driven speed of the unwind spindle). Where the unwind spindle 27 is undriven (i.e., generally free to rotate), the tension in the moving web 23b along the path P1 is a function of the rotational speed of the drive roll 31 and the inertia of the wound roll 35 and unwind spindle.

A vacuum feed roll 37, located downstream from the drive roll 31 in the machine direction MD of the system 21, is rotatably driven to further draw the continuous web 23b in the machine direction along a path P2 from the drive roll to the feed roll. Additional guide rolls 39 are positioned along the path P2 along with a load cell 41 used in a conventional manner to monitor the tension in the web 23b as the web is drawn along the path P2 from the drive roll 31 to the vacuum feed roll 37. The tension in the web 23b along the path P2 is generally a function of the rotational speed differential between the driven vacuum feed roll 37 and the drive roll 31. It is contemplated that a suitable tension control, such as another dancer roll, a festoon or other suitable control may also be disposed intermediate the drive roll 31 and the vacuum feed roll 37 instead of or in addition to the load cell 41.

Driven rotation of the vacuum feed roll 37 feeds the continuous web 23b, still under tension, to a cutting station, indicated generally at 43, of the web handling system 21. The cutting station 43 suitably comprises a knife roll 45 and a rotatably driven anvil roll 47, with one or more cutting mechanisms (e.g., cutting blades) disposed on the knife roll for cutting the continuous web 23b into discrete webs 23a (broadly, discrete segments) at regular intervals. That is, the length of the discrete web 23a at the cutting station (referred to further herein as the "cut length" of the discrete webs of elastic material) is generally dependent on the driven rotational speed of the anvil roll 47, the vacuum level of the anvil roll and the speed of the feed roll 37, and where more than one anvil is used it is also dependent on the spacing between anvils. Thus, the cut length may be preset by the operator of the web handling system 21 by setting the anvil roll 47 rotational speed, vacuum level, and/or feed roll rotational speed, or it may be controlled by a suitable speed control (not shown) based on a predetermined target cut length. The machine direction MD path along which the web 23b is moved from the vacuum feed roll 37 to the anvil roll 47 is identified as path P3 in FIG. 1.

The term "length" as used in reference to the web 23b, or discrete web 23a (i.e., discrete segment), of elastic material refers to the length thereof in the machine direction MD, i.e., the direction in which the web is stretched prior to and then retracted subsequent to cutting and/or processing. The length does not necessarily refer to the longest planar dimension of the discrete web 23a after cutting (or discrete segment of a continuous web after processing). For example, for some side panels the continuous web 23b is moved in the machine direction MD such that immediately after cutting the longer dimension is in the cross-machine direction (i.e., the width of the web as the web is delivered to the cutting station 43). In other words, the cut length is shorter than the width of the web at the time of cutting. The discrete web 23a is subsequently rotated before being placed on the training pants assembly so that as placed on the assembly the longer dimension of the discrete web extends lengthwise of the pants. The drive roll 31, vacuum feed roll 37 and anvil roll 47 together broadly define herein a delivery system that is operable to unwind the continuous web 23b from the wound roll 25 and deliver the continuous web to the cutting station 43.

A vacuum transfer roll 49 receives the discrete webs 23a from the anvil roll 47 after cutting and transfers the discrete webs onto a suitable transfer device, such as a vacuum conveyor 50, for transport in the machine direction MD away from the cutting station. Additional transfer devices (not shown) further transport the discrete webs 23a to the manufacturing line 29, and more suitably in the illustrated embodiment to a side panel fastening station 51 where the discrete webs are placed on and assembled with (e.g., adhered or bonded to) other components of the absorbent garment assembly 52 moving along the manufacturing line. For some absorbent garments, such as training pants, the absorbent garment assembly 52 is further moved by the manufacturing line 29 to a garment fastening station 53 where the side panels at front and back waists of the garment are secured together to form a three-dimensional article having a continuous waistline in the manner of underwear.

One or more detection or monitoring systems for detecting and determining the length (and hence subsequent recovery) of the discrete webs 23a at particular locations or at a time t after cutting are disposed at predetermined locations, such as intermediate the vacuum transfer roll 49 of the web handling system 21 and the side panel fastening station 51 of the manufacturing line 29. For example, in the illustrated embodiment a first inspection system 55, and more suitably a vision inspection system, is located downstream (in the machine direction MD) from the vacuum transfer roll 49 at a first distance therefrom and a second inspection system 57, also more suitably a vision inspection system, is located downstream from the first inspection system such as at or adjacent to the side panel fastening station 51 to determine the length of the discrete web 23a as the web approaches the fastening station or just after the discrete web (i.e., the side panel material) has been secured to the moving absorbent garment assembly 52.

The machine direction MD distances between the various components and stations of the web handling system 21 and manufacturing line 29 illustrated in FIG. 1 are not necessarily to scale but are otherwise generally indicative of the relative spacing between such components. Thus, given the speed of the moving web 23b (which may be monitored by various speed sensors, not shown, disposed along the paths P1, P2 or at other locations along the web handling system 21) and the known machine direction MD distance between any two stations or system components, the time that the web takes to reach any particular station or component may be readily determined. The time t may also, or alternatively, be monitored or detected by suitable timing devices.

During operation of the illustrated web handling system 21, the continuous web 23b may experience various levels of tension for certain periods of time prior to reaching the cutting station 43 (or other processing station), each of which has a bearing on the elastic and visco-elastic behavior of the discrete webs 23a (i.e., discrete segments) after leaving the cutting station (i.e., the processing station). For example, while on the wound roll 25, the continuous web 23b is subjected to both radial and circumferential stresses that contribute to what is referred to herein as a wound off tension (i.e., the tension in the continuous web as the web is unwound from the wound roll during operation).

Figure 1A:
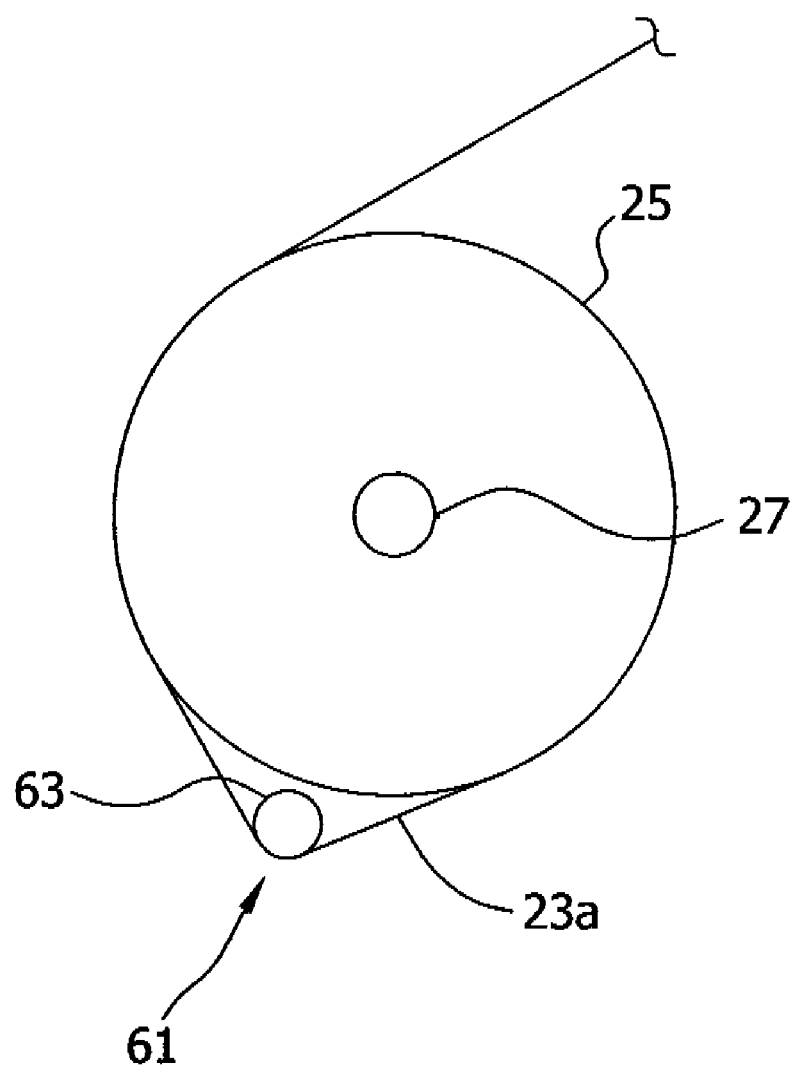
FIG. 1A is a schematic of an unwind spindle, wound roll of web material and a wound off tensioning monitoring system of the web handling system of FIG. 1.

In one particularly suitable embodiment the wound off tension may be determined by a suitable wound off tension monitoring system, generally indicated as 61 in FIG. 1A, as the web 23b is unwound from the wound roll 25. For example, the illustrated wound off tension monitoring system 61 comprises a load cell 63 (similar to the load cell 41 used to determine the tension in the web along path P2 in the system 21 of FIG. 1) located within the wound roll 25 between the outermost wind and the immediately underlying wind of the continuous web 23b. The load cell 63 measures the tension in the outermost wind (which is about to be wound off from the roll 25) in pounds. Dividing this tension by the average thickness and average width of the web determines the wound off stress, in pounds per square inch, of the continuous web.

In alternative embodiments, the wound off tension may be pre-determined, such as during initial winding of the continuous web 23b onto the wound roll 25 or on a separate winding system (not shown) disposed offline from the web handling system 21, to develop a wound off tension profile in which the wound off tension is recorded as a function of the radius of the wound roll 25 or as a function of the linear location along the length of the continuous web 23b on the wound roll. In such an embodiment, the wound off tension monitoring system 61 may comprise a suitable device (not shown) for monitoring the radius of the wound roll 25 and/or the linear location of the web 23b along the wound roll.

The continuous web 23b is subsequently subjected to a first moving tension for the period of time during which the web is drawn along the path P1 from the wound roll 25 to the drive roll 31, and is subjected to a second moving tension for the additional period of time during which the web is drawn along the path P2 from the drive roll to the vacuum feed roll 37. The continuous web 23b is also subjected to a third moving tension, based on a speed differential between the anvil roll 47 and the vacuum feed roll 37, as well as the respective vacuum levels of the vacuum feed roll and the anvil roll, for a relatively short period of time as the web moves along the path P3 from the vacuum feed roll to the anvil roll. It is understood that once the web 23b is cut into the discrete webs 23a there is a substantially reduced tension (and in some embodiments, zero tension) applied to each discrete web (i.e., the discrete web of elastic material is allowed to recover) depending on subsequent processing of the web after cutting, such as, for example, the level of vacuum applied to the web by a vacuum conveyor that transfers the discrete webs away from the cutting station.

With reference back to FIG. 1, the illustrated web handling system 21 further comprises a control system 71 for controlling operation of the web handling system. The control system 21 may be part of, or may provide input to and receive feed back from, a manufacturing control system (not shown) of the manufacturing line 29 to which the discrete webs are supplied for incorporation into the absorbent garment. The control system 71 is suitably in communication with the various operating components of the system 21 and is capable of monitoring and adjusting (or causing to be adjusted) various operating parameters of the system 21 (as indicted by the arrows drawn between the control system and the respective operating components in FIG. 1) such as the speeds of the drive roll 31, vacuum feed roll 37 and other transfer devices to thereby control the machine direction MD speed of the continuous web 23b (to the cutting station 43) and discrete webs 23a (downstream of the cutting station); the tension in the web 23b along paths P1, P2 and P3, and/or the cut length of the discrete webs at the cutting station. The control system 71 also suitably communicates with and receives input from the wound off tension monitoring system 61, the load cell 63 and the inspection systems 55, 57. The control system 71 may suitably comprise a control circuit, a computer that executes control software, a programmable logic controller and/or other suitable control devices.

In accordance with one embodiment of a method for controlling the length of the discrete web 23a (i.e., a discrete segment) of elastic material at a time t after the web is cut from the continuous web 23b of the elastic material (or, more broadly, at a time t after the discrete segment is processed at a particular processing station), the control system 71 is used to control the various operating components of the web handling system 21 so as to control the length of the discrete web after it is cut (i.e., after the discrete segment leaves the processing station). More suitably, the control system 71 is configured to control the length of the discrete web 23a according to a feed-forward type control method. According to such a method, a recovered length of the discrete web 23a at a time t after it is cut from the continuous web 23b of material is predicted at least in part as a function of the wound off tension of the wound roll 25 and of the time t at which a target recovered length is to be achieved.

For example, in the illustrated embodiment the length of the discrete web 23a is predicted (based on the wound off tension) at a time t after cutting, wherein the time t corresponds to the location of the side panel fastening station 51 where the side panels overlay and are secured to the moving absorbent garment assembly 52. The time t corresponding to this location is simply a function of the machine direction MD distance from the cutting station 43 to the side panel fastening station 51 and the speed at which the discrete webs 23a are moved therebetween, which may be a manual input to the control system or may be monitored by the control system 71.

Even more suitably, the length of the discrete web 23a at a time t after it is cut from the continuous web 23a of elastic material at the cutting station 43 is predicted according to the following algorithm which is programmed into the control system 71:

$$\text{Strain} = (C_0 + C_1 * \tau + C_2 * \tau^2) * [J_0 + J_1 * e^{(t/T1)} + J_2 * e^{(t/T2)}]$$

where;

τ=the wound off tension (lbs.)

t=time after cut (seconds)

Ji are coefficients based on a recovery curve of the discrete web, which is a curve fit of the measured length of a discrete web after cut versus time t after the cut for the particular web handling system parameters at which the wound roll is processed;

Ci are coefficients based on the spread of multiple recovery curves for different wound off tensions (i.e., each wound off tension generates a different recovery curve and the Ci coefficients model the spread between these recovery curves); and Ti are time related constants based on the different curve fit patterns at different times after the cut.

In one particularly suitable embodiment, the coefficients Ji, Ci and Ti are constants determined by conducting data collection and curve fitting off-line (i.e., other than on the manufacturing line 29 and more suitably other than on the web handling system 21). For example, by knowing (or assuming) 1) the speed at which the continuous web 23b moves along the various paths P1, P2, P3, 2) the distance of each of these paths, and 3) the various tensions to which the continuous web is subjected as the web moves along each of the paths, and assuming that these are held constant, the data for determining the coefficients for the above algorithm (as they relate to the particular web speeds, distances and tensions) can be measured using suitable off-line measuring equipment (not shown). Without limitation, the following is one example of how these coefficients may be determined offline.

EXAMPLE 1

The following example determines the coefficients Ji, Ci and Ti using an offline data collection process. The data collected in this example assumes a web handling system 21 substantially as set forth above and illustrated in FIG. 1 in which the discrete webs 23a of elastic material are used as side panels that are subsequently secured to a moving absorbent garment assembly 52 at a side panel fastening station 51 to further assemble the absorbent garment. The continuous web 23b of elastic material for this example is a continuous web of vertical filament material having a basis of weight of about 108.87 grams per square meter (gsm).

A vertical filament laminate (VFL) is a composite material having at least two layers in which one layer is a gatherable layer and the other layer is an elastic layer. The layers are joined together when the elastic layer is extended from its original condition so that upon relaxing the layers, the gatherable layer is gathered. The composite may be stretched to the extent that the non-elastic material gathered between the bond locations allows the elastic material to elongate. One type of vertical filament laminate is disclosed, for example, by U.S. Pat. No. 6,916,750 to Thomas et al., the content of which is incorporated herein by reference in its entirety. In particular, the VFL used for this example is that used as side panel material for training pants made by Kimberly-Clark Worldwide, Inc., Neenah, Wis.

The web 23b has a uniform caliper (i.e. thickness) of about 0.03 inches and a uniform width of about 12.13 inches. The continuous web 23b is assumed (based on actual runtime data from the web handling system 21 or estimated based on desired operating parameters such as web speed and tension to achieve a cut length at the cutting station 43 of about 3.414 inches) to have 1) a first tension along path P1 of about 0.83 lbs. for a period of about 10 seconds (e.g., as the web moves from the wound roll 25 to the drive roll 31), 2) a second tension along path P2 of about 1.1 lbs. for a period of about 4 seconds (e.g., as the web moves from the drive roll to the vacuum feed roll 37, and 3) a third tension along path P3 of about 1.54 lbs. for a period of about 0.5 seconds (e.g., as the web moves from the vacuum transfer roll to the anvil roll 47 for cutting).

Five different data collection runs are made, with the wound off tension being the only variable that changed for each run. In particular, the wound off tension is 0.5, 1.0, 1.5, 2.0 and 2.5 lbs. for each respective run. It is understood, however, that more or less runs may be made by increasing or decreasing the number of wound off tension increments, or by increasing the overall range of the wound off tension.

Suitable measuring equipment comprises conventional modulus test machine in which a sample length of the web material is held fixed at one end and is attached to a rail mounted, low friction slide. The tension machine is capable of controlling the position of the slide on the rail to adjust the tension, and hence the elongation, in the web. For each data collection run, the sample is cut from the roll and allowed to come to equilibrium in an untensioned state. The web is then tensioned in accordance with the simulated wound off tension for that run (e.g., 0.5 lbs. for the first run, 1.0 lbs. for the second run, etc.) and held at this tension for a period of one-hour to simulate the effects of the radial and circumferential stresses experienced by a wound web for prolonged periods. The slide is then adjusted to tension the web at the first tension (0.83 lbs.) for 10 seconds, then at the second tension (1.1 lbs.) for 4 seconds, and finally at the third tension (1.54 lbs) for 0.5 seconds to simulate movement of the web through the web handling system 21 from the wound roll 25 to the cutting station 43.

The slide is then released to move freely on the tension machine rails so that no tension is applied to the web. The web is thus allowed to recover in order to model the elastic and visco-elastic behavior of the discrete webs 23a after being cut at the cutting station 43. The recovered length of the web (and more suitably the change in length, or shrinkage of the web, reported as strain) is periodically monitored and recorded, e.g., every 10 seconds, for a total period of 60 seconds. The procedure is conducted for each of the other four runs to model the other wound off tensions.

Figure 4:
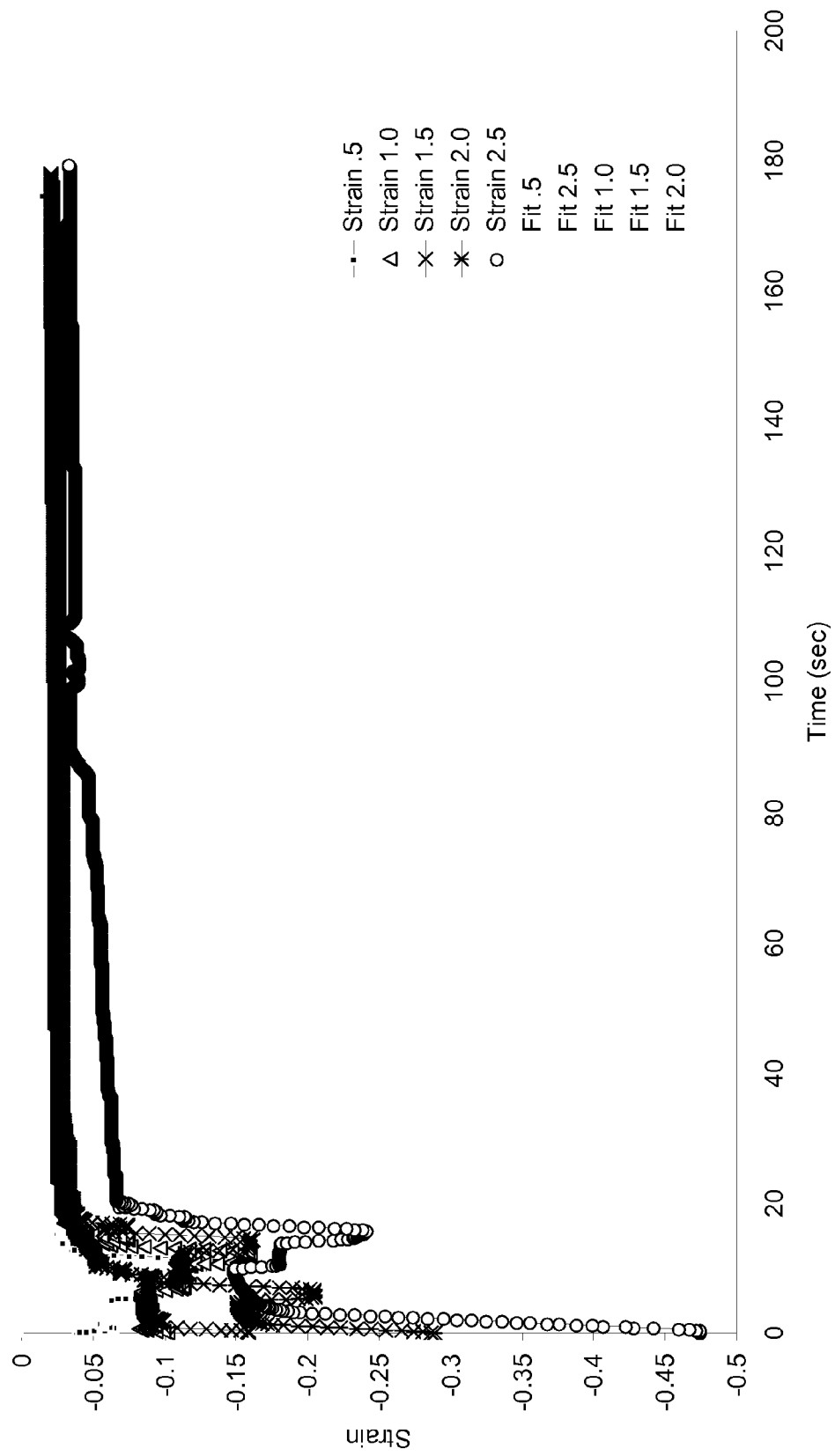
FIG. 4 is a plot of recovery curves of the measured strain versus time at zero tension (i.e., after the simulated cut of a discrete segment from a continuous web) for a simulated processing of a continuous web of elastic material.
Figure 5:
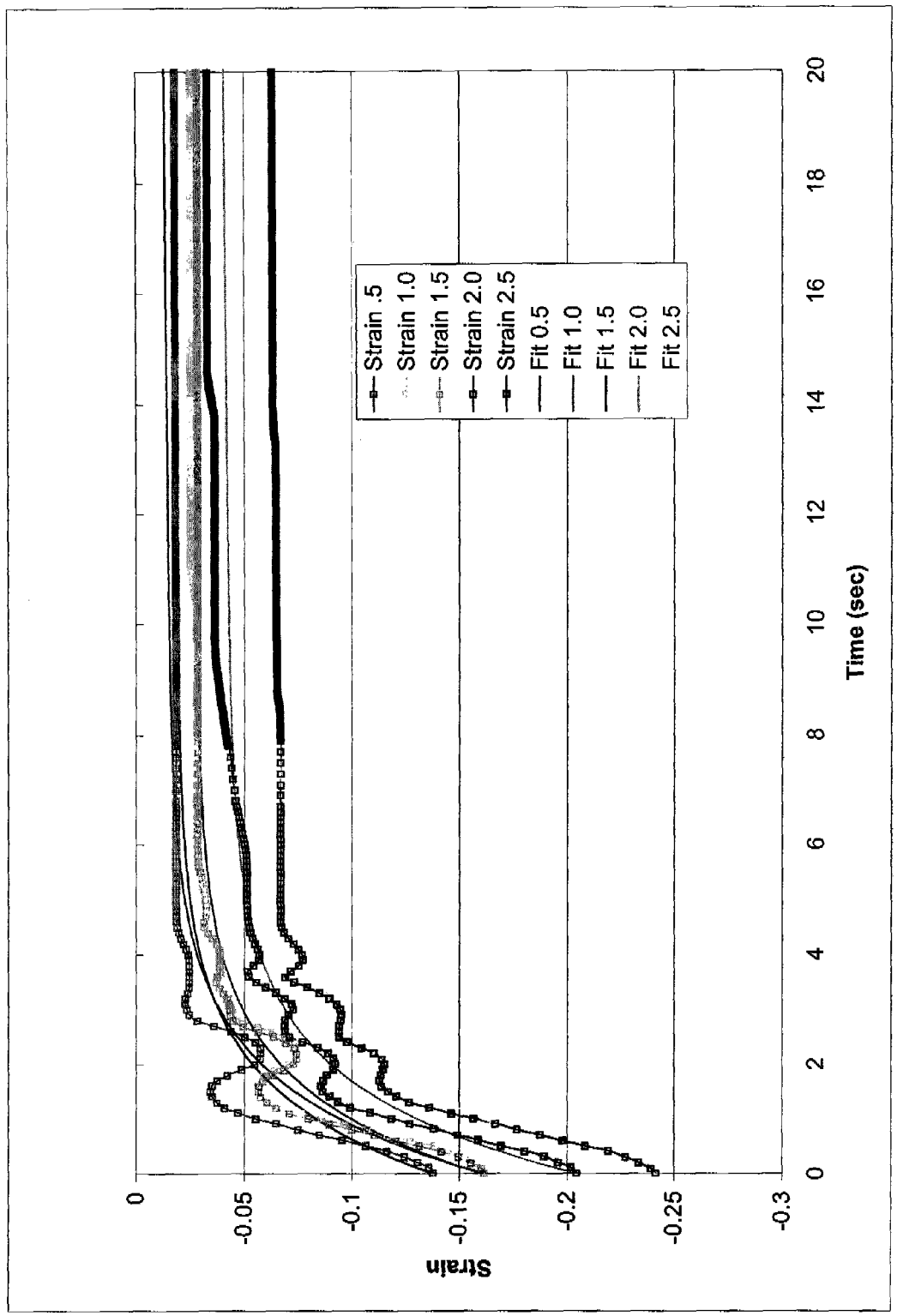
FIG. 5 is the same plot as FIG. 4 but over a shorter time duration after the simulated cut.

FIG. 4 is a set of recovery curves, overlaid curve fits, of the measured strain versus time at zero tension (i.e., after the simulated cut) for each of the runs. FIG. 5 is the same plot but over a shorter time duration after the simulated cut. The coefficients Ji, Ci and Ti are determined from the curve fits of the recovery curves for each wound off tension and from the spread between the curve fits. Any conventional curve fitting software may be used to curve fit the data and to determine the needed coefficients.

Inserting these coefficients into the above algorithm yields an algorithm that can used to model the behavior of the discrete webs 23a (i.e., to predict the length, such as the recovered length, of the discrete webs) formed by the operating web handling system at a time t after the web is cut from the tensioned continuous web 23b at the cutting station 43. Using this algorithm, the recovered length of the discrete web 23a at a time t after cutting is thus a direct function of the wound off tension of the wound roll 25 and of the time t after the discrete web is cut at the cutting station 43. The recovered length of the discrete web 23a, using the algorithm, is also indirectly a function of the particular operating parameters (i.e., web speeds, continuous web tensions and cut length) used in determining the coefficients (the constants) of the algorithm.

In the illustrated embodiment, an operator 73 uses a suitable input device 75 to input parameters needed by the control system 71 to control the recovered length of the discrete webs 23a at a time t after cutting. The input device 75 in this instance is a computer keyboard associated with a personal computer (PC) system that is part of or interfaces with the control system 71 of the web handling system 21.

Input supplied to the control system 71 by the operator 73 includes, at a minimum, a target recovered length of the discrete web 23a at a predetermined location downstream of the cutting station 43, such as the side panel fastening station 51 in the illustrated embodiment, and the coefficients, or constants to be used in the above algorithm for predicting the recovered length of the discrete web at the predetermined location. Additionally, the operator 73 may input a suitable tolerance range for the recovered length, i.e., the acceptable range of recovered lengths of the discrete webs 23a at the predetermined location downstream of the cutting station 43. Additional input may also include the web 23b caliper and width.

A distance of the predetermined location at which the recovered length of the discrete web 23a is to be predicted may be manually input by the operator 73, or it may be measured by suitable monitoring devices (not shown) of the web handling system 21 and/manufacturing line 29. The control system 71 may determine the time t after cutting that corresponds to the predetermined location, such as by determining the web speed of the discrete webs 23a from the cutting station 43 to the predetermined location downstream therefrom and using the web speed and distance to determine the time t to travel this distance. Alternatively, the control system may determine the time t to reach the predetermined location using suitable monitoring systems (not shown) It also contemplated that the operator 73 may instead directly input the time t at the input device 75 without departing from the scope of this invention.

Figure 2:
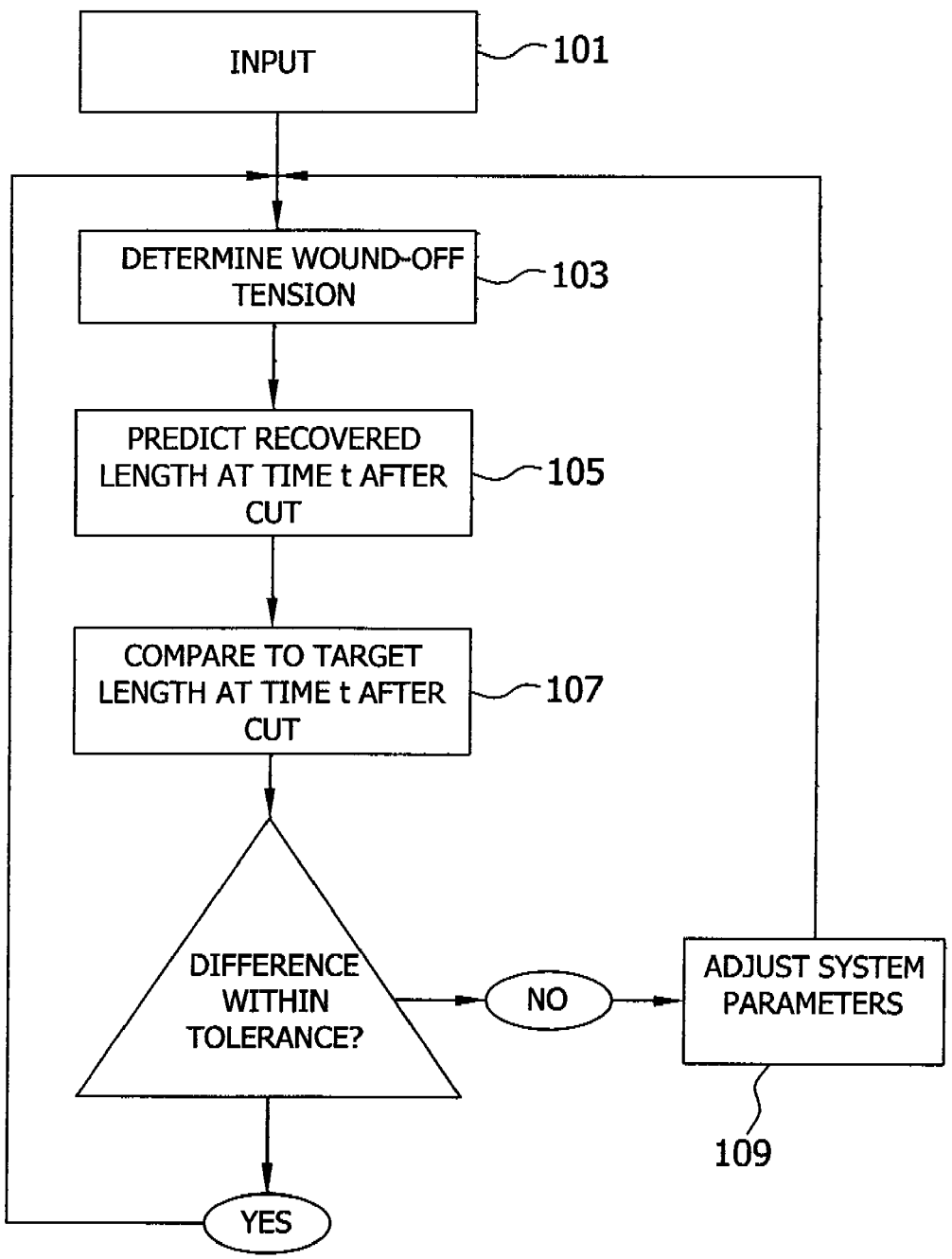
FIG. 2 is a flow diagram according to one embodiment of a method of controlling the length of a discrete web of material at a time t after being cut from a continuous web of elastic material.

With reference to FIG. 2, the above input is communicated to the control system at step 101 in accordance with one method for controlling the recovered length of the discrete web 23a after cutting (broadly, after leaving a particular processing station). Where an active wound off tension monitoring system 61 is provided as illustrated in FIG. 1A, the wound off tension is periodically determined by the monitoring system, such as about every 10 seconds for example, and the data is relayed at 103 to the control system 71. Alternatively, a predetermined data table of wound off tension to wound roll radius (or other suitable wound roll parameter) may be input to the control system 71 by the operator 73, such as by using the input device 75 or suitable electronic communication device. In such an embodiment, a suitable monitoring device (not shown) may be used to intermittently determine the radius (or other parameter) of the wound roll 25 and communicate such data to the control system 71, which then determines the wound off tension based on the predetermined wound off tension data table.

With the wound off tension and the time t as inputs to the algorithm, the control system 71 uses the algorithm to predict (at step 105) the recovered length of the discrete web 23a at the time t after the discrete web is cut from the continuous web 23b. The control system then compares the predicted recovered length to the input target recovered length at step 107 to determine a difference therebetween. If the difference between the predicted recovered length and the target recovered length is within the input tolerance range, no adjustments to the operating parameters of the web handling system 21 are needed.

Where the differential falls outside the tolerance range, one or more of the web handling system operating parameters, such as one or more of the web speeds, one or more of the web tensions, and/or the cut length at the cutting station, is adjusted by the control system 71 at step 109 to thereby adjust the recovered length of the discrete web 23a at the time t following cutting, i.e., before the segments of the web that are being wound off from the wound roll are processed (i.e., cut) at the cutting station. For example, where the predicted recovered length exceeds the target recovered length, one or more of the web speeds may be decreased and/or one or more of the web tensions may be decreased to shorten the cut length at the cutting station 43 so that the recovered length will also decrease. Alter-natively, the web speeds and/or tensions may be adjusted to increase the tension (and hence the elongation) in the continuous web 23b at the cutting station 43 (e.g., without necessarily changing the cut length) to increase the amount of recovery and thereby decrease the recovered length at the time t after the cut.

Where the predicted recovered length is shorter than the target recovered length, the web 23b speeds and/or web tensions and/or cut length are increased to increase the cut length to thereby increase the recovered length of the discrete webs 23a, or the web speeds and/or tensions may be adjusted to decrease the tension in the web at the cutting station 43 (while the cut length remains generally unchanged) to decrease the amount of recovery and thereby increase the recovered length of the discrete web at the time t after the cut. As the wound roll 25 is unwound, the wound off tension will vary and thus the web handling system 21 operating parameters may be repeatedly modified by the control system 71 as the wound off tension changes.

Thus, in accordance with the feed-forward control, the control system 71 determines the needed cut length (or discrete length) and/or operating parameter adjustments while the continuous web is upstream from the cutting station (i.e., the particular processing station of interest), based on the predicted recovered length, so that upon recovery for a time t downstream of the cutting station 43 (i.e., the particular processing station) the recovered length of the discrete web 23a (i.e., the discrete segment) will match the target recovered length.

It is understood that by changing the web speed and/or the web tension at one or more of the intervals (paths P1, P2, P3) from the wound roll 25 to the cutting station 43, i.e., these parameters may become different from those used to obtain the data upon which the coefficients input by the operator were based. As a result, the coefficients used as input to the algorithm may not sufficiently model the revised web speeds and/or tensions.

Figure 3:
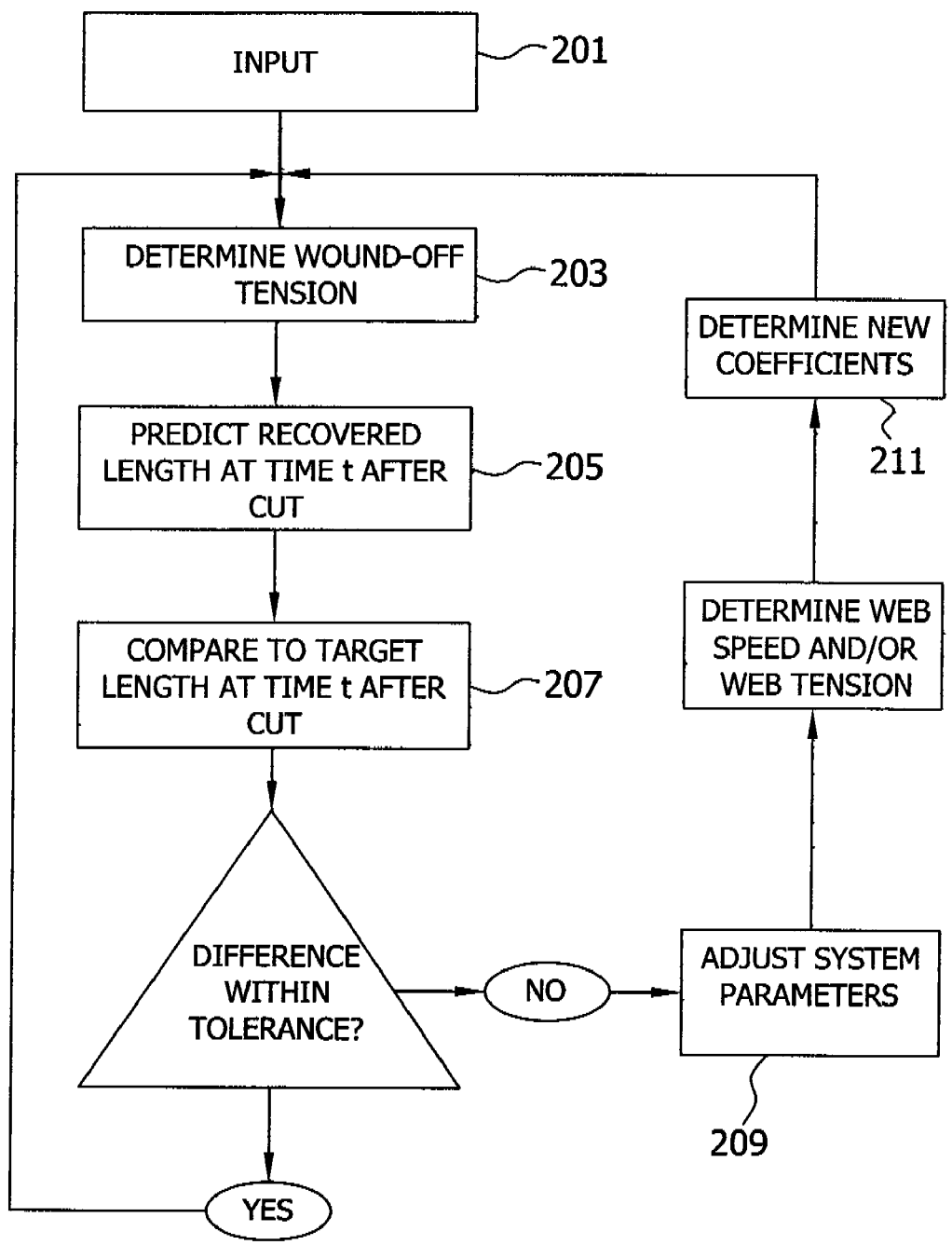
FIG. 3 is a flow diagram according to a second embodiment of a method of controlling the length of a discrete web of material at a time t after being cut from a continuous web of elastic material.

To this end, it is contemplated that coefficient data may be compiled as in the above Example by running the data collection for different web speeds and tensions along one or more of the paths P1, P2, P3 of the web handling system. Thus, in a second embodiment of method of controlling the recovered length of a discrete web after being cutting from a continuous web of elastic material, illustrated in FIG. 3, the input 201 may further include a "look-up" table of coefficients where the proper coefficients to use in the algorithm are a function of the current web speeds and/or tensions at one or more of the paths P1, P2, P3. That is, the web speeds and/or web tensions may be monitored by the control system 71 and, when changed such as at step 211 in response to the predicted recovered length being undesirably different from the target recovered length, used by the control system to adjust the coefficients used in the algorithm to further predict 205 the recovered web length at the time t after cutting.

Alternatively, it is contemplated that the above Example offline data collection process may be used with one or more of the web tensions (e.g., along the paths P1, P2, P3) as variables and being varied during different runs of the data collection process along with the wound off tension. As a result, an algorithm that models the recovered length of the discrete web 23a at a time t after cutting as a direct function of the wound off tension and one or more of the web tensions along the paths P1, P2, P3 may be used by the control system 71 to predict the recovered length of the discrete webs at time t after cutting.

It is also contemplated that the control system 71 may operate to collect additional, real-time data relating the actual recovered length (as measured, for example, by the inspection system 57 at the side panel fastening station 51) at a time t after cutting to at least the wound off tension of the wound roll. In such an embodiment, real-time curve fits of the data can be made by the control system 71 and the input coefficients to the algorithm adjusted accordingly. Such a method allows for variations in different webs, i.e., the elastic and viscoelastic behavior between different webs is accounted for in real-time (i.e. without the need for off-line data collection for each different wound roll of elastic material). Alternatively, or additionally, the actual recovered length could be used as an input to the control system and used to further determine needed adjustments of the various process parameters.

When introducing elements of the present invention or preferred embodiments thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions and methods without departing from the scope of the invention, it is intended that all matter contained in the above description and shown in the accompanying drawings shall be interpreted as illustrative and not in a limiting sense.

What is claimed is:

1. A method of controlling the length of a discrete segment of an elastic web in a web handling system, said method comprising:
   unwinding a continuous web of elastic material from a wound roll of said continuous web;
   determining a wound off tension of said continuous web as said continuous web is being unwound from said wound roll;
   delivering the unwound continuous web in a machine direction from said wound roll to a processing station while maintaining the web in tension for at least part of the distance traveled by the web from the wound roll to the processing station, a discrete segment of the web having a segment length at said processing station;
   transporting the discrete segment of the web away from the processing station along said machine direction for at least a time t wherein the discrete segment decreases in machine direction length from said segment length to a recovered length after leaving said processing station;
   predicting, based at least in part on said wound off tension of said continuous web, the recovered length of the discrete segment at said time t after leaving the processing station; and
   controlling, in response to the predicted recovered length of the discrete segment, at least one of 1) the speed at which the continuous web is delivered from the wound roll to the processing station, 2) the tension in the continuous web as the web is delivered from the wound roll to the processing station, and 3) the segment length of the discrete segment at the processing station.

2. The method set forth in claim 1 further comprising comparing the predicted recovered length of the discrete segment to a predetermined target recovered length of the discrete segment at said time t after leaving the processing station, the controlling step comprising controlling, in response to said comparison of the predicted recovered length of the discrete segment to the predetermined target recovered length of the discrete segment, at least one of 1) the speed at which the continuous web is delivered from the wound roll to the processing station, 2) the tension in the continuous web as the web is delivered from the wound roll to the processing station, and 3) the segment length of the discrete segment at the processing station.

3. The method set forth in claim 2 wherein the comparing step comprises determining the difference between the predicted recovered length of the discrete segment and the predetermined target recovered length of the discrete segment at said time t after leaving the processing station, and comparing the difference therebetween to a target tolerance range for said difference, the controlling step comprising controlling, in response to said difference falling outside of said target tolerance range, at least one of 1) the speed at which the continuous web is delivered from the wound roll to the processing station, 2) the tension in the continuous web as the web is delivered from the wound roll to the processing station, and 3) the segment length of the discrete segment at the processing station.

4. The method set forth in claim 1 wherein the step of delivering the unwound continuous web in a machine direction from said wound roll to said processing station comprises maintaining the continuous web of elastic material in tension for substantially the entire distance from the wound roll to the processing station.

5. The method set forth in claim 4 wherein the tension in said continuous web of elastic material is non-uniform along the distance from the wound roll to the processing station.

6. The method set forth in claim 1 wherein the predicting step comprises predicting a recovered length of the discrete segment at said time t after leaving the processing station based at least in part on said wound off tension of said continuous web and said time t after the discrete segment leaves the processing station.

7. The method set forth in claim 6 wherein the predicting step comprises predicting the recovered length of the discrete segment at said time t after the discrete segment leaves the processing station based at least in part on said wound off tension of said continuous web, the tension of the web along at least a portion of the distance that the continuous web is delivered from the wound roll to the processing station, and said time t after discrete segment leaves the processing station.

8. The method set forth in claim 1 wherein the wound off tension is determined by measuring the tension in the continuous web as it is being wound off of the wound roll.

9. The method set forth in claim 1 further comprising the step of determining, prior to unwinding the continuous web from said wound roll, a relationship between the wound off tension of the wound roll and at least one of the radius of the wound roll and the linear location along the wound roll, the step of determining the wound off tension comprising determining said at least one of the radius of the wound roll and the linear location along the wound roll as the wound roll is being unwound and determining the wound off tension based on said at least one of the determined radius of and the determined linear location along the wound roll.

10. The method set forth in claim 1 wherein the processing station comprises a cutting station, the discrete segment comprising a discrete web cut from the continuous web at said cutting station and having a cut length at said cutting station, said transporting step comprising transporting the discrete web away from the cutting station along said machine direction for at least a time t after cutting wherein the discrete web decreases in machine direction length from said cut length to a recovered length after cutting, said predicting step comprising predicting, based at least in part on said wound off tension of said continuous web, the recovered length of the discrete web at said time t after cutting, and said controlling step comprising controlling, in response to the predicted recovered length of the discrete web, at least one of 1) the speed at which the continuous web is delivered from the wound roll to the cutting station, 2) the tension in the continuous web as the web is delivered from the wound roll to the cutting station, and 3) the cut length of the discrete web at the cutting station.

11. The method set forth in claim 1 further comprising the steps of determining an actual recovered length of the discrete segment at or after said time t after leaving the processing station, comparing the actual recovered length of the discrete segment to a predetermined target recovered length of the discrete segment at the time at which the actual recovered length is determined, and controlling in response to said comparison of the actual recovered length to the predetermined target recovered length of the discrete segment, at least one of 1) the speed at which the continuous web is delivered from the wound roll to the processing station, 2) the tension in the continuous web as the web is delivered from the wound roll to the processing station, and 3) the segment length of the discrete segment at the processing station.

* * * * *